United States Patent [19]

Tarancon

[11] Patent Number: 5,482,682
[45] Date of Patent: Jan. 9, 1996

[54] APPARATUS FOR DIRECT FLUORINATION OF A HYDROCARBON BY MOLECULAR FLUORINE GAS

[75] Inventor: Gregorio Tarancon, High Springs, Fla.

[73] Assignee: Florida Scientific Laboratories Inc., High Springs, Fla.

[21] Appl. No.: 63,941

[22] Filed: May 17, 1993

[51] Int. Cl.$^6$ .................. B01J 8/04; C08F 2/00; C07C 17/20

[52] U.S. Cl. .......... 422/189; 422/131; 422/188; 422/196; 570/170

[58] Field of Search .................. 422/131, 132, 422/134, 138, 187, 188, 189, 193, 196; 570/170; 239/86; 366/167, 173

[56] References Cited

U.S. PATENT DOCUMENTS

| | | | |
|---|---|---|---|
| 1,990,692 | 2/1935 | Henne | 570/170 |
| 2,005,706 | 6/1935 | Daudt et al. | 570/170 |
| 2,935,513 | 5/1960 | Takeba et al. | 422/188 |
| 3,693,656 | 9/1972 | Sauer | 366/167 |
| 3,779,518 | 12/1973 | Koepke et al. | 366/167 X |
| 3,843,546 | 10/1974 | Sabolev et al. | 570/170 |
| 4,091,403 | 5/1978 | Ohsaka et al. | 570/170 |
| 4,114,195 | 9/1978 | Dirksing et al. | 366/167 |
| 4,680,406 | 7/1987 | Fujioka | 570/170 |
| 4,855,112 | 8/1989 | Adcock | 422/189 |
| 4,885,416 | 12/1989 | Mader | 570/170 |
| 5,011,293 | 4/1991 | Roop et al. | 366/173 |

*Primary Examiner*—Robert J. Warden
*Assistant Examiner*—Christopher Y. Kim
*Attorney, Agent, or Firm*—Ezra Sutton

[57] ABSTRACT

The present invention relates to a method and apparatus for direct fluorination of hydrocarbons (having 1 to 4 carbons) by using molecular fluorine gas in a liquid medium. The number of reactors or reaction steps is a function of the number of hydrogen atoms in the hydrocarbon to be replaced by molecular fluorine to produce a refrigerant or other product.

19 Claims, 7 Drawing Sheets

APPARATUS FOR DIRECT FLUORINATION OF A HYDROCARBON BY MOLECULAR FLUORINE GAS

FIELD OF THE INVENTION

The present invention relates to a method and apparatus for direct fluorination of hydrocarbons (1 to 4 carbons) by using molecular fluorine gas in a liquid medium. The number of reactors or reaction steps is a function of the number of hydrogen atoms in the hydrocarbon to be replaced by molecular fluorine to produce a refrigerant.

BACKGROUND OF THE INVENTION

This invention deals with a method and apparatus to produce HCF's and CF's non-restricted with the potential of being substitutes for the restricted refrigerants used at the present time. The prior art teaches some methods used in the preparation of fluorocarbons and hydrofluorocarbons and, in general, the preparation of chlorofluorocarbons and chlorohydrofluorocarbons. However, the presence of by-products is one of the main considerations in the selection of the method and apparatus for the manufacturing process. See John D. Calfee and Lucius A. Bigelow, J. Am. Chem. Soc. 59 (1937) 2072 disclosed in the series of papers, "The Action of Elemental Fluorine on Organic Compounds," IV The Vapor Phase Fluorination of Ethane. It discloses hydrogen substitution by fluorine, as well as chlorine substitution by fluorine. The apparatus described is considered today a typical vapor phase reactor for the fluorination of organic compounds.

In a continuation of the series "The Action of Elementary Fluorine Upon Organic Compounds," Eduard A. Tyczkowski and Lucius A. Bigelow introduce the jet fluorination reactor. The jet, venturi or adductor reactor used in the prior art, is a combustion chamber in which the hydrocarbon acts as the fuel and the fluorine as the oxidizer. A mixture of several fluorinated products is obtained when jet vapor fluorination is conducted. Recently, jet fluorination was proposed in a liquid phase, but apparently, several problems arose in the suction portion of the venturi where the reaction takes place. Apparently, because fluorine is highly reactive, it was difficult to control the reaction, which resulted in inconsistent products and malfunction of the apparatus.

Accordingly, it is an object of the present invention to provide fluorinated hydrocarbons by using an apparatus and method in which the reaction is controllable and the desired fluorinated product is obtainable without product deterioration and without undesired by-products.

It is another object of the invention to provide a method and apparatus for the fluorination of hydrocarbons for replacement of the restricted halocarbons, such as freon, that cause ozone depletion.

It is another object of this invention to provide the method and apparatus for the purification of the fluorinated hydrocarbons.

It is another object of the invention to provide a contacting zone or reaction vessel where the interactive effect takes place in the area of contact of the two reactants, fluorine and hydrocarbon. The two reactants contact and react with each other in a medium of liquid solvent, which acts as a heat sink to prevent the overheating effect of the high rate of the reaction.

It is another object of the invention to provide a tubular reactor with a laminar flow of solution fluid to prevent any back mixing of the fluid. The laminar flow without the back mixing prevents undesired by-product formation.

It is another object of the invention to provide a fluorination reactor with one or more fluorine feeder injectors to produce fluorinated compounds from one fluorine in the molecules to perfluorinated molecules.

It is another object of the invention to provide a separation stage for the removal of dry hydrogen fluoride as a secondary product. The dry hydrogen fluoride is a source of raw material in fluorine electrolysis and can be reused.

It is another object to provide a closed system which produces the desired final product, with a minimum of by-product produced, and wherein the solvent is reused, and the hydrogen fluoride by-product may be reused in fluorine electrolysis.

SUMMARY OF THE INVENTION

The present invention provides a method and apparatus for the direct fluorination of organic compounds, and more specifically, the fluorination of hydrocarbons within (1 to 4 carbons) a liquid medium. The apparatus includes at least three vessels: the interacter vessel, the thermobath vessel, the gas vessel, and the solubilizer vessels. One solubilizer vessel is used to dissolve or blend the fluorine with the fluorinated solvent, and the other solubilizer vessel is used to dissolve the hydrocarbon to be fluorinated with the fluorinated solvent. Each interacter vessel has at least two connections to feed the fluorine solution and the hydrocarbon solution. The number of interacter vessels and the number of solubilizer vessels for fluorine solution are increased to replace additional hydrogen atoms by fluorine in the hydrocarbon.

In its broad aspect, the method and apparatus of the present invention provides fluorination and purification of hydrocarbons by mixing molecular fluorine with fluorinated liquid solvent in a solubilizer fluorine vessel, mixing hydrocarbon with fluorinated liquid solvent in a solubilizer hydrocarbon vessel, injecting these into an interacter fluorination reactor, where the solution of fluorine liquid solvent contacts the solution of hydrocarbon liquid solvent, and the two solutions interact together and the reaction is initiated. The fluorinated liquid solvent is inert to fluorine under the process condition of temperature and fluorine concentration. The operating temperature is, in general, around the boiling point of the fluorinated liquid medium.

BRIEF DESCRIPTION OF THE DRAWINGS

Further objects, features, and advantages of the present invention will become apparent upon consideration of the detailed description of the presently-preferred embodiment, when taken in conjunction with the accompanying drawings wherein.

DESCRIPTION OF THE PREFERRED EMBODIMENT

The presence of chlorine, bromine, or iodine in halocarbons implies a severe restriction on handling imposed by the Environmental Protection Agency in regards to atmospheric damage when they are disposed of. The era of using these compounds as refrigerants or chemical intermediaries ended with the Montreal protocol. In the present invention, the refrigerant replacement is free of chlorine, bromine, or iodine, and the reactants are free of chlorine, bromine, or iodine. According to the present invention, hydrocarbons (1 to 4 carbons) are fluorinated by direct fluorination with molecular fluorine that only contain carbon, hydrogen, and fluorine or carbon and fluorine.

The principal group of hydrocarbons used in this invention for the preparation of refrigerants are methane, ($CH_4$), ethane ($C_2H_6$) propane ($C_3H_8$) and butane ($C_4H_{10}$). By using the method and apparatus of this invention, some of the final products produced are:

| R-23  | Fluoroform         | $CHF_3$    |
|-------|--------------------|------------|
| R-152 | Difluoroethane     | $C_2H_4F_2$ |
| R-143 | Trifluoroethane    | $C_2H_3F_3$ |
| R-134 | Tetrafluoroethane  | $C_2H_2F_4$ |
| R-125 | Pentafluoroethane  | $C_2HF_5$  |
| R-227 | Heptafluoropropane | $C_3HF_7$  |
| R-116 | Hexafluoroethane   | $C_2F_6$   |
| R-218 | Perfluoropropane   | $C_3F_8$   |

Figure 1:
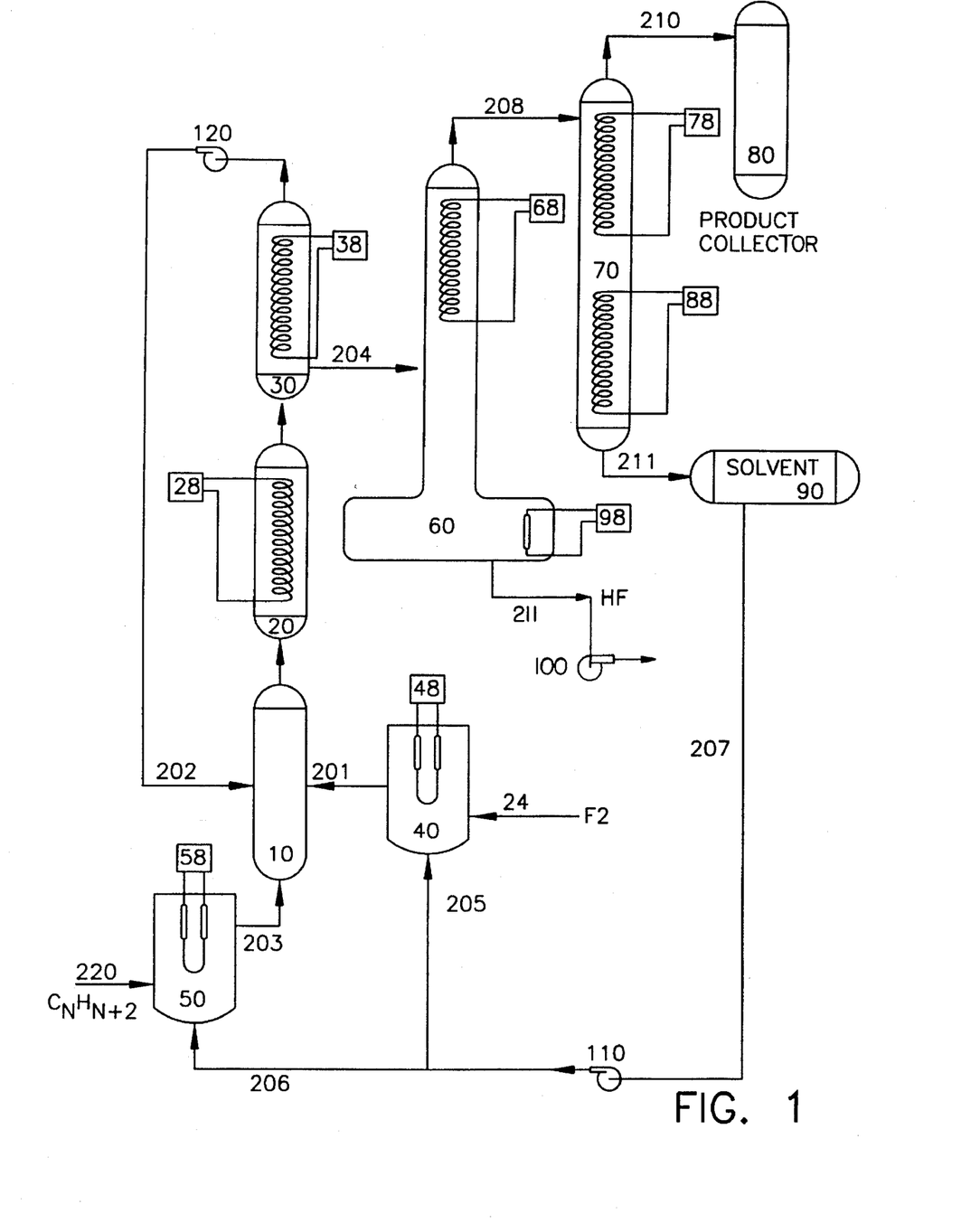
FIG. 1 is a schematic diagram of the apparatus of the present invention.

The method and apparatus of the invention is to produce perfluoroethane, perfluoropropane, perfluorobutane, and hydrofluorocarbons. The fluorination reactor 10 consists of a tubular reactor with multifeed points for fluorine solution and a single feed for the hydrocarbon, such as ethane, propane, or butane solution. The reactor has as many cooling zones as the fluorine solution feeds. Each fluorine solution feed corresponds to a predetermined concentration and is prepared in its own fluorine solvent mixer. The fluorination apparatus has as many fluorine solvent mixers as fluorine solution feeders in the reactor. The fluorine solution mixer consists of a tank with a cooling medium for removing the heat of solution of fluorine in contact with the fluorinated solvent. The fluorine is preferably injected into the bottom portion of the tank, as well as the fluorinated solvent. The fluorine solution travels along the fluorine solution mixer, and cooling is provided by a cooling medium. The fluorine solution mixture is withdrawn from the fluorine solution mixer from a connection opposite to the fluorine injection. FIG. 1 is an illustration of a mixer 40 of the invention apparatus. One of the fluorinated solvents used in the invention illustration is perfluoropropane. The fluorine solvent mixer 40 has an injection port for fluorine and an injection port for perfluoropropane (solvent).

Equipment and Components

The apparatus in FIG. 1 illustrates a process plant, which consists of an interacter 10, a thermobath tubular reactor 20, a fluorine solubilizer 40, a hydrocarbon solubilizer 50, a condenser 30, a hydrogen fluoride separator 60, a product extractor 70, a product receiver 80, a solvent receiver 90, a solvent recycle pump 110, a compressor for gas recycle 120, and a hydrogen fluoride pump 100. The solvent recycle pump 110 discharges the fluid to the solvent feeder 205 and solvent feeder 206 for reuse. The fluorine feed 24 in solubilizer 40 is dissolved with solvent supplied 205. Fluorine is dissolved in the solution in the solubilizer 40. The hydrocarbon supplied to solubilizer 50 is dissolved with the solvent supplied by 206. The hydrocarbon is dissolved in the solution in the solubilizer 50. The fluorine solution feeder 201 and the hydrocarbon solution feeder 203 operate at the same discharge pressure. The fluids from feeder 201 and from feeder 203 interact in the interacter 10, where the main portion of the reaction takes place. The velocity of the combined flows from 201 and from 203 is sufficiently fast that the heat dissipation takes place in the body of the solution in the thermobath 20. In the bottom portion of the interacter 10 is the recycle feeder 202, which assists the fast displacement of the solution to the thermobath 20.

The solubilizer 40 is cooled by a cooling medium 48, so that the temperature is maintained lower than the minimum temperature of reaction between fluorine and the solvent. The solubilizer 50 is cooled by a cooling medium 58, so the temperature is maintained lower than the minimum temperature of reaction between fluorine and the solvent. The cooling medium may be a coil of $CO_2$ liquid, glycol water, or a refrigerant system. The diameter of reactor 10 is sufficiently large to maintain laminar flow along the reactor from the bottom to the liquid discharge 204. Any residual unreacted gas, hydrocarbon, fluorohydrocarbon, or fluorine saturated with solvent flows to the condenser 30 where the solvent is condensed and the non-condensable parts are accumulated in the gas portion of the condenser 30. The unreacted vapor from the top of the condenser 30 is recycled by compressor 120 to the interacter 10 via line 202. The condenser 30 has a cooling medium 38 for the cooling and condensation of any vapor condensable at the operating temperature.

The liquid solution 204 discharged through 204 is fed into a separator 60 where the hydrogen fluoride is extracted and discharged through line 211 by the pump 100. The solution free of hydrogen fluoride is transferred to separator 70, from the top of separator 60, by using the line 208. In the separator 70, the purified product is extracted at the top by using line 210 and is supplied to product collector 80, and at the bottom of 70, the solvent is transferred to solvent receiver 90 through line 211. The solvent in receiver 90 is recycled back to the solubilizers 40 and 50 by using line 205, 206, 207, and pump 110. The separator 70 has at least one cooling medium 78 and at least one heater 88. The separator 60 has at least one heater 98 and at least one cooling medium 68. The separator 60 and separator 70 are standard distillation equipment and are considered as part of standard engineering practice but are essential in this method and apparatus invention.

FIGS. 3 to 6 are illustrations of the typical apparatus of the invention for the fluorination of hydrocarbons. FIGS. 5A, 5B, and 5C illustrate different forms of the interacter 10, which, in this case, is a "T" with injector feeders. The selection of a "T" is for simplicity, but other geometrical shapes may be used. The embodiments shown in FIGS. 5A, 5B, and 5C each have at least two feeder ports 12 and 14, one for the fluorine solution and the other for the hydrocarbon solution, and one discharge port 16. The feeder ports normally have an injector 18 to increase the velocity for the dynamic interaction. The discharge port 16 of the "T" is the outlet or connection to the thermobath 20 where the fluid is changed to a laminar flow.

Figure 6A:
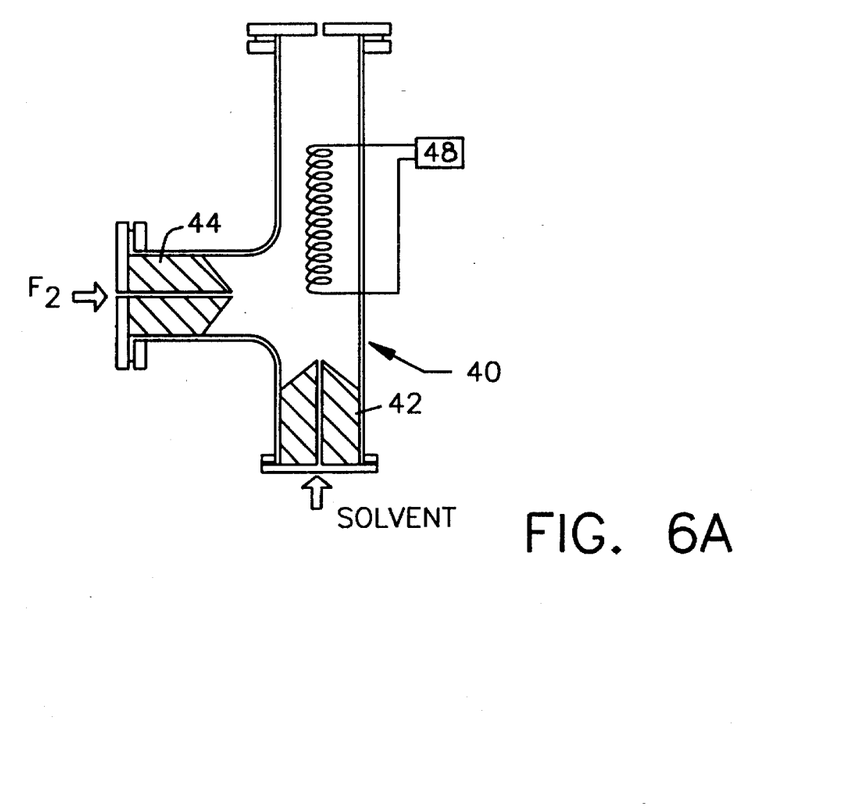
FIGS. 6A and 6B show the solubilizer vessels for the fluorine and hydrocarbon.
Figure 6B:
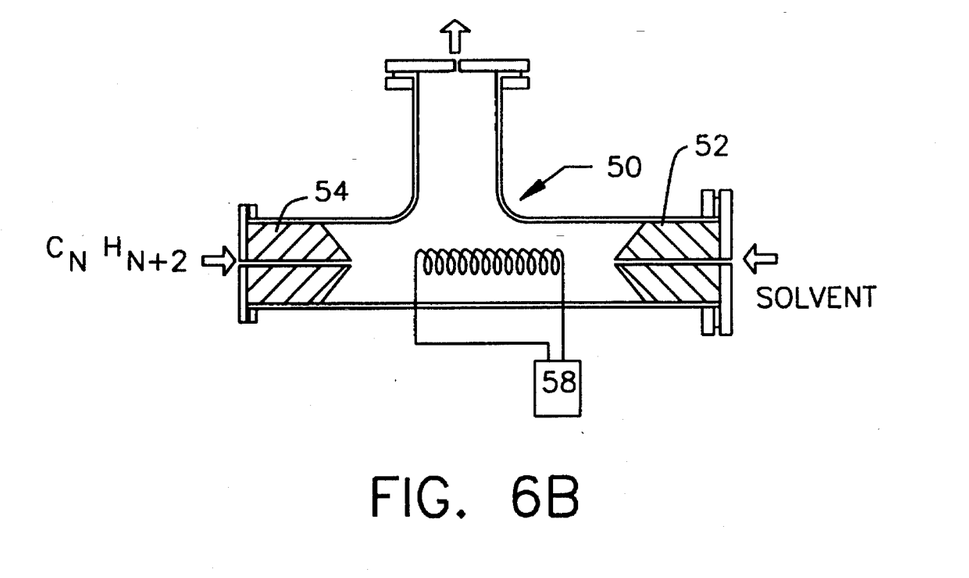

FIGS. 6A and 6B show solubilizers 40 and 50, which are "T"-shaped with injector feeders 42 and 52 for the solvent and injectors 44 and 54 for fluorine and for hydrocarbon. The solubilizer 40 has a cooling medium 48, and the solubilizer 50 has a cooling medium 58 to maintain the temperature at the desired condition.

Figure 5A:
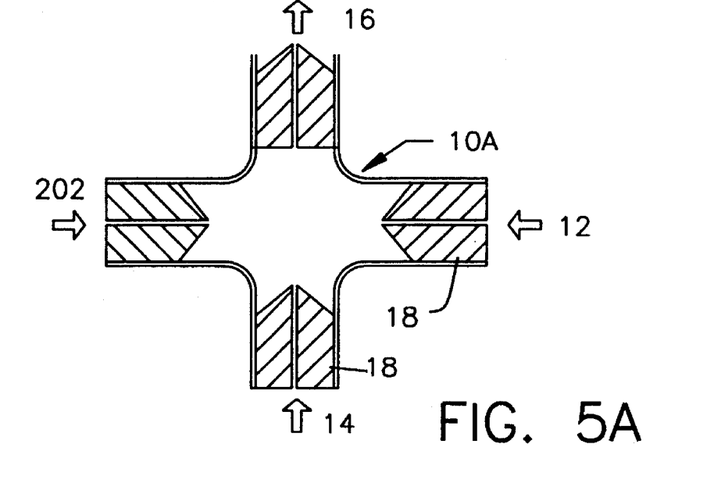
FIGS. 5A, 5B, and 5C show alternative arrangements of the interacter or mixer vessel.
Figure 5B:
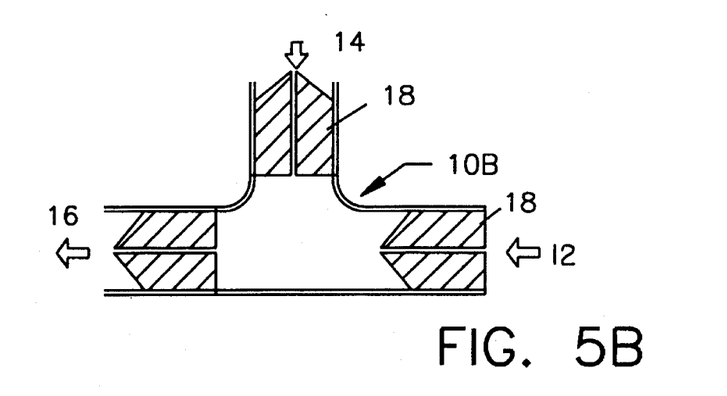
Figure 5C:
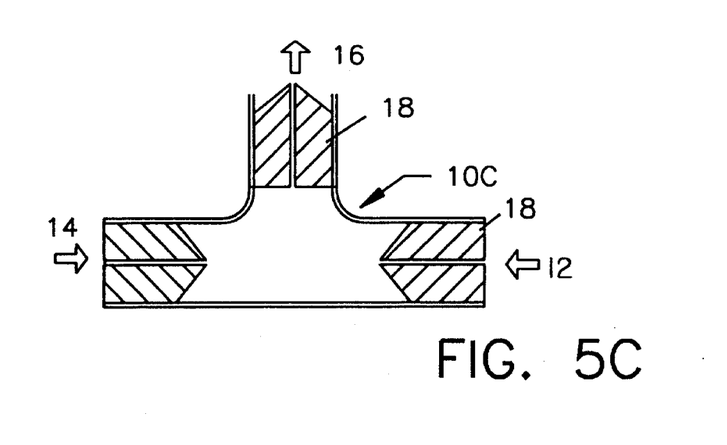
Figure 8:
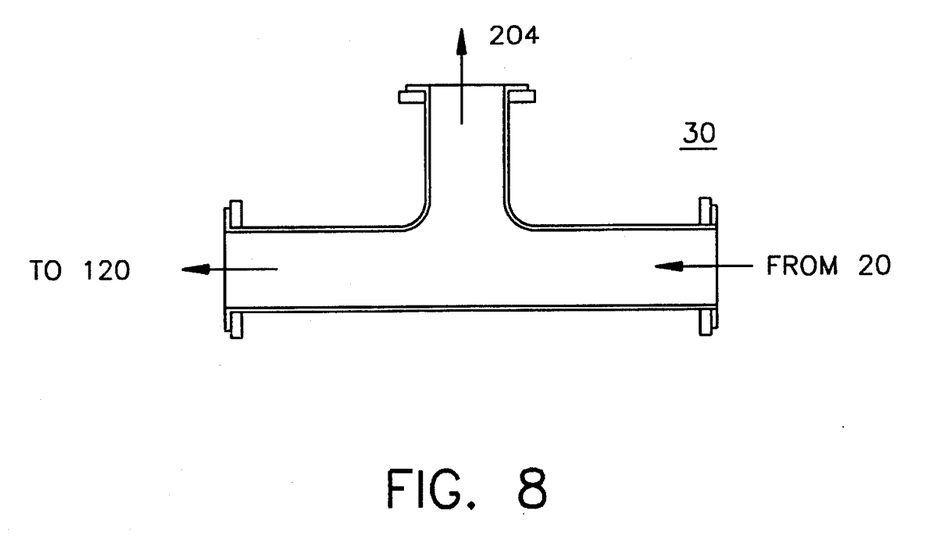
FIG. 8 shows the condenser.

FIG. 8 is an illustration of the gas condenser 30, where one branch 204 is the discharge to the separator, and the other branch 120 is the gas recycle port. Three of the four main components of the apparatus invention in illustrations FIGS. 5, 6, and 8 are "T"-type units. The "T" type of solubilizer and the "T" type of interacter 10 characterize the apparatus for the fluorination of hydrocarbons in a liquid solvent medium.

Figure 2:
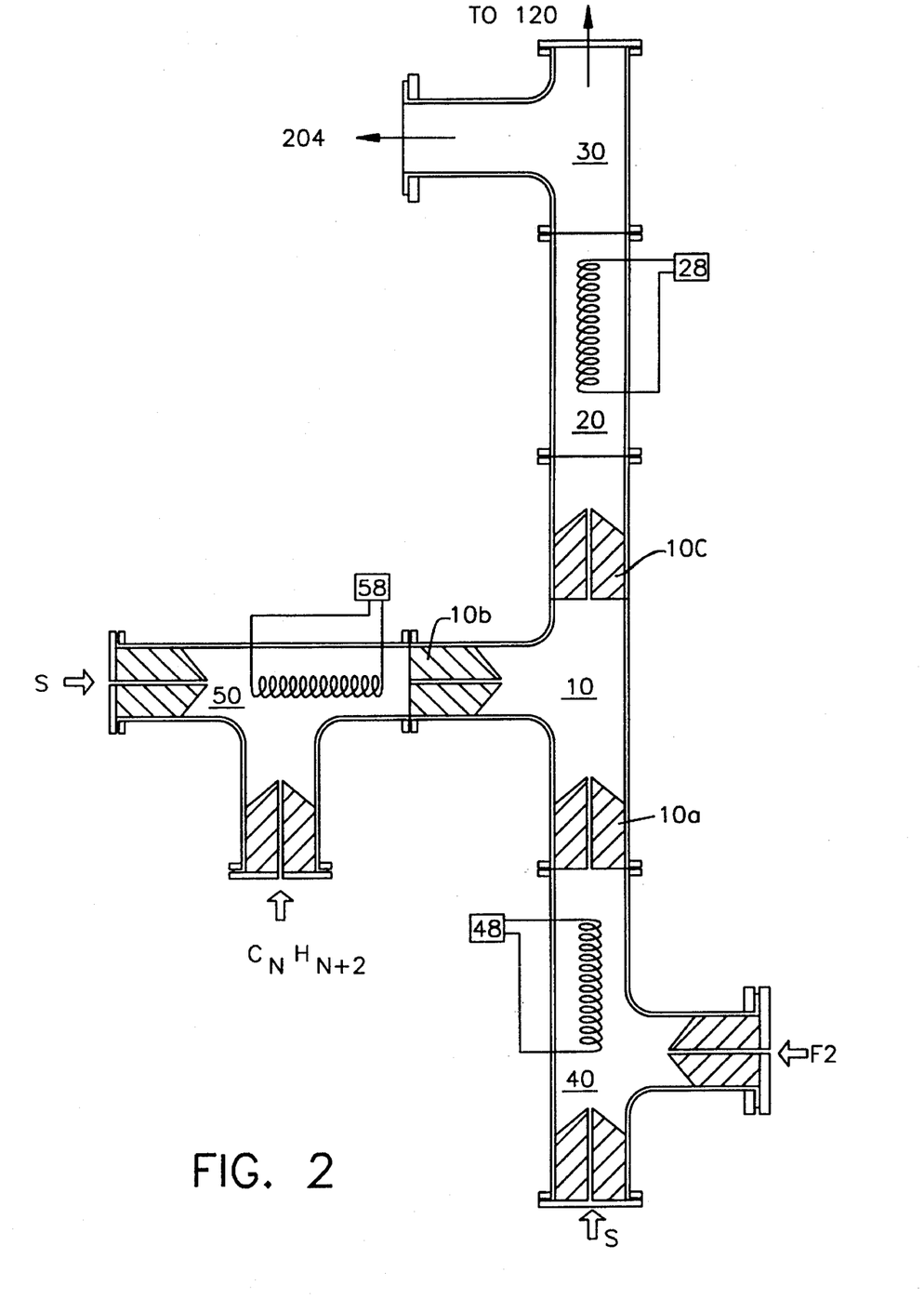
FIG. 2 shows the vessels interconnected.
Figure 7:
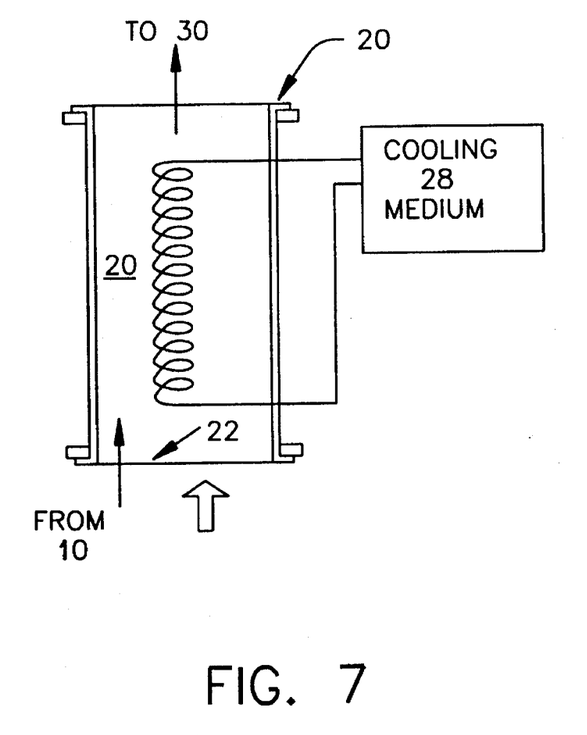
FIG. 7 shows the thermobath unit.

FIG. 7 is an illustration of the thermobath unit 20 used as part of the "T" fluorination apparatus of FIG. 2. The thermobath is a pipe 20 with a cooling medium 28, sufficiently large in diameter that the fluid is in laminar flow. Any heat from the reaction mainly produced in the corresponding interacter 10 is removed by the cooling medium 28 of the thermobath 20. The dynamic interaction of the ingredients in the interacter 10 produce a uniform solution at the entering point 22 of the thermobath 20, and the uniformity of the overall composition will not mitigate from one point of the thermobath to another point, because the fluid is in laminar flow.

Figure 3:
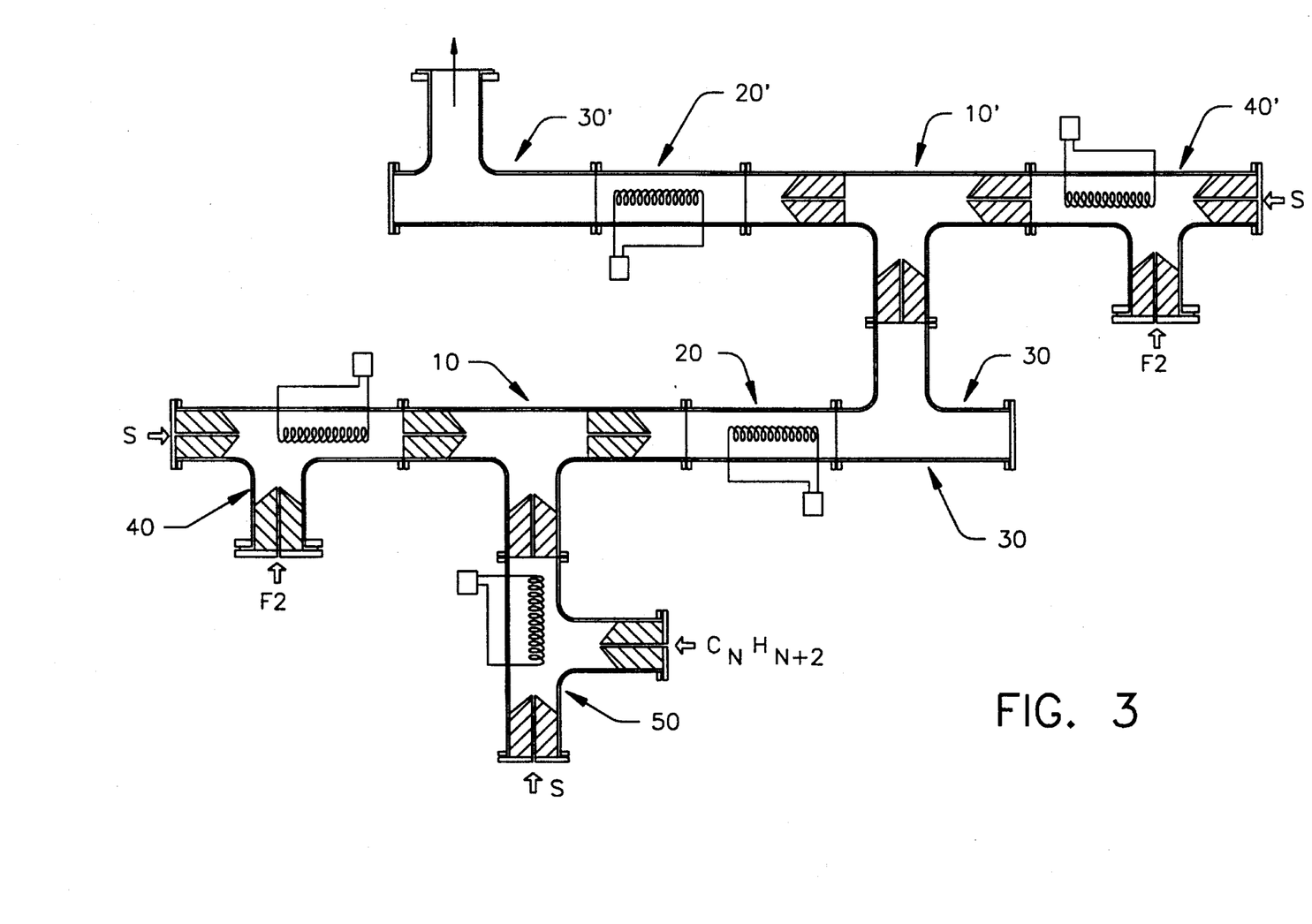
FIG. 3 shows the present invention in a two-stage arrangement, wherein there is a second stage to replace a second hydrogen atom in the hydrocarbon with fluorine.
Figure 4:
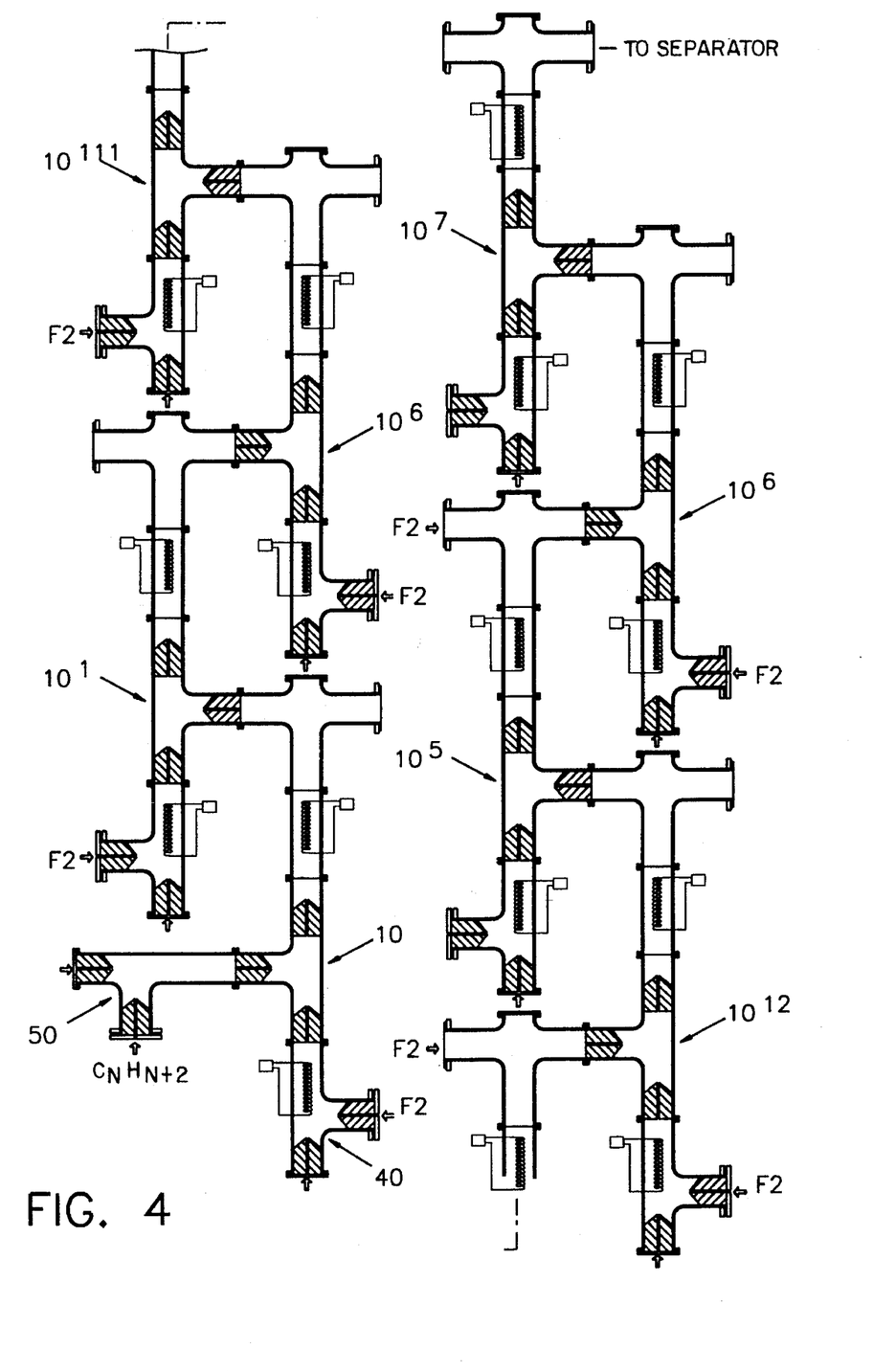
FIG. 4 shows an eight-stage arrangement, wherein eight hydrogen atoms are replaced with fluorine in accordance with the present invention.

FIGS. 2 to 4 illustrate three types of arrangements of the "T" apparatus. FIG. 2 is for a single-stage vertical arrangement, FIG. 3 is for a two-stage horizonal arrangement, and FIG. 4 is for a multistage vertical arrangement. FIG. 2 illustrates a vertical arrangement with a single section and one-step fluorination. FIG. 3 illustrates two steps of fluorination. FIG. 4 illustrates multisteps of fluorination.

FIG. 2 shows the solubilizers 40 and 50 connected to reactor 10, thermobath 20, and condenser 30. In solubilizer or vessel 40, molecular fluorine gas is dissolved in liquid solvent to produce a first liquid or solution. In solubilizer 50, the hydrocarbon to be fluorinated is dissolved in a liquid solvent to produce a second liquid or solution. Reactor 10 has a first injector 10a for injecting the first liquid into it with a turbulent flow and a second injector 10b for injecting the second liquid into it with a turbulent flow, so that the first and second liquids are uniformly mixed in reactor 10 and reacted with each other to produce a reaction liquid, which is supplied to thermobath 20 by injector 10c. Thermobath 20 includes cooling medium 28 for cooling the heat of the reaction in the reaction liquid, and it produces laminar flow (as opposed to turbulent flow) of the reaction liquid through the thermobath vessel to complete the reaction. Injectors 10a and 10b are disposed at 90° relative to each other to increase the turbulent flow in reactor 10 to enhance the mixing and reaction of the first and second liquids. Condenser 30 is connected to thermobath 20 to condense any vapor, and it may include a cooling medium. Its output at 204 is supplied to separator 60. Separator 60 receives the reaction liquid and separates the HF by-product therefrom to produce the final product and solvent, which is then supplied to separator 70 for separating the final product from the liquid solvent. The final product is collected in collector 80, and the solvent is supplied to unit 90 for reuse and resupply to solubilizers 40 and 50 to provide a continuous closed system for producing the final product. Similarly, the output of condenser 30 is fed back and recycled to reactor 10 for reuse. Typically, the output of condenser 30 is gas and the unreacted fluorine and hydrocarbon. The various vessels 10, 20, 30, 40, and 50 may be stainless steel, brass, copper, monel, or other suitable materials.

In the preferred embodiments, the solvents may be perfluoropropane or perfluorobutane, and the hydrocarbon may be methane, ethane, propane, or butane.

FIG. 3 shows two stages, with an additional reactor 10', an additional fluorine solubilizer 40', an additional thermobath 20', and an additional condenser 30'. In this second stage, a second hydrogen atom in the hydrocarbon $C_N H_{N+2}$ is replaced by molecular fluorine to produce the final product.

To illustrate the ranges for the process parameters of the invention, one product will be used as an example.

FIG. 4 is an illustration of the method and apparatus for the fluorination of propane into perfluoropropane. The apparatus consists of eight fluorination steps, as shown, and in each step of the "T" apparatus, there is substituted one hydrogen of the propane molecule with fluorine. In eight steps, eight hydrogens are replaced by eight fluorines, and the propane molecule is transformed into perfluoropropane.

Each stage consists of an interacter zone 10 with a (propane/fluorinated propane-perfluoropropane) solution feeder, a (fluorine-perfluoropropane) solution feeder, and reacted solution is discharged to the thermobath zone 20. The fluorine solution of fluorine and perfluoropropane (the solvent) is prepared in the fluorine solubilizer 40 where the perfluoropropane is injected through a solvent feeder 205, and the fluorine is injected through a solute feeder 24. The fluorine as solute is dissolved in the body of perfluoropropane. The range of temperature in the fluorine solubilizer 40 is from about (−40° C. to +40° C.) and the range of pressure from about (20 psia to 200 psia). The temperature range and the pressure range in the interacter 10 for the preparation of perfluoropropane are the same in all the components. Temperature in the range of (−40° C. to +40° C.) and pressure in the range of (20 psia to 200 psia).

The propane solubilizer 50 has the perfluoropropane feeder 206 for supplying perfluoropropane to the solubilizer 50. The flow at feeder discharge 203 is in a turbulent flow condition, with the Reynolds number in the range of about from 5,000 to about 500,000. The propane is fed via 220 in a turbulent flow condition, similar to the perfluoropropane.

The fluorine solubilizers have the same design criteria as the propane solubilizer.

The interacters 10 are designed with the condition of turbulent flow, including rotational motion of the fluids. The interaction in interacters 10 between the fluids from the two feeders 40 and 50 is total. The two feeders are at 90° with respect to each other. This design condition provides rotational motion, which induces better contact of the two fluid streams and more interaction between the reactants. The thermobath 20 is designed with the condition of laminar flow to prevent back migration of the reactants and to provide enough retention time for temperature equilibrium. The Reynolds number for the thermobath zone is in the range from 15 to 1,500.

Example

An apparatus with the capacity to process 1 mole/hour of propane, uses a propane solubilizer 50 with perfluoropropane injection feed of about 836 lbs/hour, which produces a solution of 5% by weight of propane in perfluoropropane. The fluorine solubilizers 40 of each stage require an injection feed of fluorine of 1 mole/hour and perfluoropropane feed of 342 lbs/hour to produce a solution of 10% by weight of fluorine in perfluoropropane solution. Each interacter 10 of the apparatus places in contact 1 mole/hour of fluorine with 1 mole/hour of propane and generates 1 mole/hour of hydrogen fluoride. At the top of the apparatus, the amount of perfluoropropane increases by 5%. The 5% increment is the product generated in the apparatus. At the top of the apparatus, 8 moles/hour of hydrogen fluoride are in the solution. The rate of perfluoropropane production is 1 mole/hour or 188 lbs/hour. The perfluoropropane inventory in the apparatus is about 3,600 lbs.

The new method and apparatus of the present invention for the fluorination of hydrocarbons have the following advantages and benefits: the preparation of several fluorinated compounds in the same apparatus; a minimum amount of by-product is generated; a continuous operation without any difficulty; a variable capacity or rate of production, as desired; easy recovery of hydrogen fluoride with high quality for the application; and a recyclable product that meets the desired specifications.

The present invention has applications for producing refrigerants and for producing degreasing agents used for cleaning oily surfaces, and for producing plasma for use in the field of semiconductors.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. Apparatus for direct fluorination of a hydrocarbon by molecular fluorine gas, comprising:
   a) first vessel means for dissolving molecular fluorine gas in a liquid solvent to produce a first liquid;
   b) second vessel means for dissolving the hydrocarbon to be fluorinated in a liquid solvent to produce a second liquid;
   c) third vessel means connected to said first and second vessel means for receiving said first and second liquids to react with each other and produce a reaction liquid; and
   d) first injector means disposed within said third vessel means for injecting said first liquid into said third vessel means with a turbulent flow, and having second injector means disposed within said third vessel means for injecting said second liquid into said third vessel means with a turbulent flow, so that said first and second liquids are uniformly mixed and reacted with each other to produce said reaction liquid.

2. Apparatus in accordance with claim 1, further comprising a fourth vessel means connected to the output of said third vessel means for receiving said reaction liquid, said fourth vessel means including cooling means for cooling said reaction liquid and means for producing laminar flow of said reaction liquid through said fourth vessel means as said reaction liquid is cooled by said cooling means.

3. Apparatus in accordance with claim 2, wherein said third vessel means includes a third injector for injecting said reaction liquid into said fourth vessel means.

4. Apparatus in accordance with claim 2, further including a condenser connected to an output of said fourth vessel means to condense any vapor produced by the reaction of said first and second liquids, said condenser including cooling means, and an outlet for connection to a separator unit.

5. Apparatus in accordance with claim 4, further including feedback means connected to said condenser for supplying said condensed vapor to said third vessel means for reuse.

6. Apparatus in accordance with claim 1, wherein said first and second injector means are disposed at an angle relative to each other in said third vessel means to increase the turbulent flow in said third vessel means to enhance the mixing and reaction of said first and second liquids.

7. Apparatus in accordance with claim 1, wherein said first and second vessel means each include means for receiving said liquid solvent, and said liquid solvent is perfluoropropane.

8. Apparatus in accordance with claim 1, wherein said first and second vessel means each include means for receiving said liquid solvent, and said liquid solvent is perfluorobutane.

9. Apparatus in accordance with claim 1, wherein said second vessel means includes means for receiving said hydrocarbon, and said hydrocarbon is selected from the group consisting of methane ($CH_4$), ethane ($C_2H_6$), propane ($C_3H_8$), and butane ($C_4H_{10}$).

10. Apparatus in accordance with claim 1, wherein said first vessel includes a first injector for injecting said molecular fluorine gas into said first vessel means, and a second injector for injecting said liquid solvent into said first vessel means.

11. Apparatus in accordance with claim 1, wherein said second vessel means includes a first injector for injecting said hydrocarbon into said second vessel means, and a second injector for injecting said liquid solvent into said second vessel means.

12. Apparatus in accordance with claim 1, wherein said first and second vessel means each include cooling means for cooling said first and second liquids, respectively.

13. Apparatus in accordance with claim 1, further including a first separator unit for receiving said reaction liquid and for separating by-product to produce a final product and a liquid solvent.

14. Apparatus in accordance with claim 13, further including a second separator unit connected to said first separator unit for receiving and separating said final product from said liquid solvent.

15. Apparatus in accordance with claim 14, further including a final product collector connected to said second separator for collecting and storing said final product.

16. Apparatus in accordance with claim 14, further including a solvent collector connected to said second separator for collecting and storing said solvent for reuse.

17. Apparatus in accordance with claim 16, further including recycling means connected to said solvent collector for recycling said solvent and for resupplying said solvent to said first and second vessel means for reuse to provide a continuous system for producing said final product.

18. Apparatus in accordance with claim 1, further including an additional first vessel and an additional third vessel means, and the output of said third vessel means being connected to the input of said additional third vessel means to repeat the reaction process.

19. Apparatus for direct fluorination of a hydrocarbon by molecular fluorine gas, comprising:
   a) first vessel means for dissolving molecular fluorine gas in a liquid solvent to produce a first liquid;
   b) second vessel means for dissolving the hydrocarbon to be fluorinated in a liquid solvent to produce a second liquid;
   c) third vessel means connected to said first and second vessel means for receiving said first and second liquids to react with each other and produce a reaction liquid;
   d) first injector means for injecting said first liquid into said third vessel means with a turbulent flow, and having second injector means for injecting said second liquid into said third vessel means with a turbulent flow, so that said first and second liquids are uniformly mixed and reacted with each other to produce said reaction liquid; and e) at least one additional first vessel means and at least one additional third vessel means, and the output of said third vessel means being connected to the input of said at least one additional third vessel means to repeat the reaction process, wherein the number of additional third vessel means is a function of the number of hydrogen atoms in said hydrocarbon ($C_N H_{N+2}$) to be replaced by molecular fluorine to produce a final product.

* * * * *